(12) United States Patent
Xu et al.

(10) Patent No.: US 12,265,017 B2
(45) Date of Patent: Apr. 1, 2025

(54) METHOD FOR ESTABLISHING HYDROGEN CHARGING MODEL FOR PIPELINE STEEL IN EQUIVALENT WET HYDROGEN SULFIDE ENVIRONMENT AND APPLICATION THEREOF

(71) Applicant: Tianjin University, Tianjin (CN)

(72) Inventors: Lianyong Xu, Tianjin (CN); Yongdian Han, Tianjin (CN); Jiajun Shao, Tianjin (CN); Lei Zhao, Tianjin (CN); Kangda Hao, Tianjin (CN)

(73) Assignee: Tianjin University, Tianjin (CN)

( * ) Notice: Subject to any disclaimer, the term of this patent is extended or adjusted under 35 U.S.C. 154(b) by 0 days.

(21) Appl. No.: 18/818,481

(22) Filed: Aug. 28, 2024

(65) Prior Publication Data

US 2025/0076180 A1 Mar. 6, 2025

(30) Foreign Application Priority Data

Aug. 29, 2023 (CN) .......................... 202311108371.7

(51) Int. Cl.
*G01N 17/02* (2006.01)
*G16C 20/00* (2019.01)

(52) U.S. Cl.
CPC ............ *G01N 17/02* (2013.01); *G16C 20/00* (2019.02)

(58) Field of Classification Search
CPC ....... G01N 17/02; G01N 17/043; G16C 20/00
See application file for complete search history.

(56) References Cited

PUBLICATIONS

Claeys et al., "Electrochemical Hydrogen Charging of Duplex Stainless Steel," Steel & Hydrogen Section, corrosionjournal.org, 880 Aug. 2019 • vol. 75 • Issue 8 (Year: 2019).*
Lee et al., "A Theoretical Model on the Generation of the Hydrogen Induced Defects During Cathodic Charging," Scripta METALIAIRGICA, vol. 19, pp. 341-346, 1985 (Year: 1985).*
Amey et al., "Modeling Hydrogen Entry and Exit in Metals Exposed to Multiple Charging Processes," Metallurgical and Materials Transactions A, vol. 25A, Apr. 1994-723 (Year: 1994).*

(Continued)

*Primary Examiner* — Alexander S Noguerola
(74) *Attorney, Agent, or Firm* — JCIRPNET

(57) ABSTRACT

The disclosure provides a method for establishing a hydrogen charging model for pipeline steel in an equivalent wet hydrogen sulfide environment and an application thereof, which belongs to the field of corrosion electrochemistry. The method includes the following steps: using a cathode hydrogen charging method and a wet hydrogen sulfide environment method respectively to perform hydrogen charging on each sample to be tested under different reaction conditions to obtain several first hydrogen charging samples and second hydrogen charging samples; measuring the hydrogen content of each of the first hydrogen charging sample and the second hydrogen charging sample; performing curve fitting on the variables in the two methods respectively according to the obtained hydrogen content, and the hydrogen charging model for pipeline steel in the equivalent wet hydrogen sulfide environment is obtained according to the fitting result.

6 Claims, 4 Drawing Sheets

---

Use a cathode hydrogen charging method and a wet hydrogen sulfide environment method to obtain a first hydrogen charging sample and a second hydrogen charging sample

↓

Measure a hydrogen content of each of the first hydrogen charging sample and the second hydrogen charging sample

↓

Perform curve fitting on the hydrogen content obtained and obtain the hydrogen charging model for the pipeline steel in the equivalent wet hydrogen sulfide environment

(56) References Cited

PUBLICATIONS

Dmytrakh et al., "Specific Features of the Deformation and Fracture of Low-Alloy Steels in Hydrogen-Containing Media: Influence of Hydrogen Concentration in the Metal," Materials Science, vol. 54, No. 3, Nov. 2018 (Ukrainian Original vol. 54, No. 3, May-Jun. 2018) (Year: 2018).*

Feng, Pengfei, "Study on the influence of different heat treatment processes on the stress corrosion sensitivity of 35CrMo steel", CNKI Electronic Journal of Master's Degree Thesis, No. 5, May 15, 2012, with English abstract thereof, Southwest Petroleum University, pp. 1-63.

* cited by examiner

METHOD FOR ESTABLISHING HYDROGEN CHARGING MODEL FOR PIPELINE STEEL IN EQUIVALENT WET HYDROGEN SULFIDE ENVIRONMENT AND APPLICATION THEREOF

CROSS-REFERENCE TO RELATED APPLICATION

This application claims the priority benefit of China application Ser. No. 202311108371.7, filed on Aug. 29, 2023. The entirety of the above-mentioned patent application is hereby incorporated by reference herein and made a part of this specification.

BACKGROUND

Technical Field

The disclosure belongs to the field of corrosion electrochemistry, and more specifically, relates to a method for establishing a hydrogen charging model for pipeline steel in an equivalent wet hydrogen sulfide environment and an application thereof.

Description of Related Art

As important non-renewable energy sources, the development and use of oil and natural gas are closely related to lives of people. Having advantages such as safety, efficiency, and convenience, pipeline transportation is the most important type of long-distance energy transportation. As the main carrier of pipeline transportation, the safety performance assessment of pipeline steel has become a hot issue. $H_2S$ is a common gas in oil and gas transportation. Generally speaking, the gas is not very corrosive, but is easily soluble in water to form an acidic solution, causing corrosion of pipelines. Corrosion and protection in wet hydrogen sulfide environments are also considered to be the primary safety factors that petrochemical devices should consider.

The wet hydrogen sulfide environment defined in the NACE MR0175-2015 "Metallic Materials Resistant to Sulfide Stress Cracking of Oilfield Equipment" standard of the American Association of Corrosion Engineers is: (1) Acid gas system: total gas pressure≥0.4 MPa, and $H_2S$ partial pressure≥0.0003 MPa; (2) Acidic multiphase system: when the crude oil to be treated contains two or three phases (oil, water, and gas), the conditions can be relaxed to: total gas phase pressure≥1.8 MPa and $H_2S$ partial pressure≥0.0003 MPa; when the gas phase pressure is ≤1.8 MPa and the $H_2S$ partial pressure is ≥0.07 MPa; or the gas phase $H_2S$ content exceeds 15%. Currently, most of the experimental methods used to assess hydrogen damage adopt the simulated wet hydrogen sulfide environment recommended in the standard, that is, at 24±3° C., the sample is immersed in NACE-A solution (5% NaCl and 0.5% $CH_3COOH$ aqueous solution by mass), $H_2S$ gas with a partial pressure of 100 KPa is introduced, hydrogen is pre-charged for 4 days, and the test is carried out in the environment. However, the wet hydrogen sulfide environments in which pipeline steels are actually in service are different. In addition, the above test method is cumbersome and has high operational requirements. The $H_2S$ gas used is highly toxic, which poses great risks to the safety of test personnel and the environment, thereby it is inconvenient to carry out research.

SUMMARY

In view of the related art, the purpose of the disclosure is to provide a method for establishing a hydrogen charging model for pipeline steel in an equivalent wet hydrogen sulfide environment and an application thereof, which aims to solve the problems of cumbersome steps, high operating requirements, and poor safety of the existing pipeline steel hydrogen damage assessment method.

To achieve the above purpose, according to an aspect of the disclosure, a method for establishing a hydrogen charging model for pipeline steel in an equivalent wet hydrogen sulfide environment is provided, and the establishment method includes the following steps:

S1: The cathode hydrogen charging method and the wet hydrogen sulfide environment method are used respectively to perform hydrogen charging on each sample to be tested under different reaction conditions to obtain a plurality of first hydrogen charging samples and second hydrogen charging samples.

S2: The hydrogen content of each of the first hydrogen charging sample and the second hydrogen charging sample is measured.

S3: According to the hydrogen content obtained in Step S2, curve fitting is performed on the variables in the two methods respectively, and according to the fitting results, a hydrogen charging model for pipeline steel in an equivalent wet hydrogen sulfide environment is obtained.

As further preferred, in Step S1, the method for obtaining the sample to be tested is: a plurality of test samples are taken from the pipeline steel, and it is ensured that the thickness direction of each of the test samples is parallel to the diameter direction of the pipeline steel during sampling. Then, the test samples are ultrasonically cleaned in acetone and anhydrous ethanol to obtain the samples to be tested.

As further preferred, in Step S1, the sample to be tested is pretreated before oxygenation, specifically: a surface of the sample to be tested is connected to a wire, and another surface is polished. Then, the whole is sealed, and only the polished surface and the wire connector are exposed.

As further preferred, in Step S1, the cathode hydrogen charging method is specifically: the sample to be tested as a cathode is placed in an electrolyte solution, and cathode hydrogen charging is performed at a preset hydrogen charging time and current density.

As further preferred, in Step S1, the wet hydrogen sulfide environment method is specifically: the sample to be tested is placed in a test solution in a closed environment, and hydrogen sulfide gas is introduced into the test solution at a preset hydrogen charging time and hydrogen sulfide concentration so as to implement hydrogen charging in the wet hydrogen sulfide environment.

As further preferred, in Step S2, an electrochemical method is adopted for measuring the hydrogen content, specifically: the anode current change of the sample not charged with hydrogen is measured, and used as the background current curve; then, the anode current change of each of the first hydrogen charging sample and the second hydrogen charging sample under the same conditions is tested respectively, and performed interpolation calculation with the area of the background current curve to obtain the hydrogen content of each of the first hydrogen charging sample and the second hydrogen charging sample.

As further preferred, in Step S3, the least square method is used to perform curve fitting.

As further preferred, in Step S3, the hydrogen charging model for pipeline steel in an equivalent wet hydrogen sulfide environment is specifically:

$$\begin{cases} C_{H1} = A_1 t_1^{0.5} + B_1 i^{0.5} + C_1 \\ C_{H2} = A_2 t_2^{0.5} + B_2 C_{H2S}^{0.5} + C_2 \end{cases}$$

In the formula, $C_{H1}$ is the hydrogen concentration of the first hydrogen charging sample obtained by the cathode hydrogen charging method, $A_1$, $B_1$, and $C_1$ are the corresponding coefficients of the fitting surface in the cathode hydrogen charging method, $t_1$ is the hydrogen charging time of the cathode hydrogen charging method, i is the current density of the cathode hydrogen charging method, $C_{H2}$ is the hydrogen concentration of the second hydrogen charging sample obtained by the wet hydrogen sulfide environment method, $A_2$, $B_2$, and $C_2$ are the corresponding coefficients of the fitting surface in the wet hydrogen sulfide environment method, $t_2$ is the hydrogen charging time of the wet hydrogen sulfide environment method, and $C_{H2S}$ is the hydrogen sulfide concentration of the solution in the wet hydrogen sulfide environment method.

According to another aspect of the disclosure, a hydrogen charging model for pipeline steel in an equivalent wet hydrogen sulfide environment established by the above method is provided, and the model is specifically:

$$\begin{cases} C_{H1} = A_1 t_1^{0.5} + B_1 i^{0.5} + C_1 \\ C_{H2} = A_2 t_2^{0.5} + B_2 C_{H2S}^{0.5} + C_2 \end{cases}$$

In the formula, $C_{H1}$ is the hydrogen concentration of the first hydrogen charging sample obtained by the cathode hydrogen charging method, $A_1$, $B_1$, and $C_1$ are the corresponding coefficients of the fitting surface in the cathode hydrogen charging method, $t_1$ is the hydrogen charging time of the cathode hydrogen charging method, i is the current density of the cathode hydrogen charging method, $C_{H2}$ is the hydrogen concentration of the second hydrogen charging sample obtained by the wet hydrogen sulfide environment method, $A_2$, $B_2$, and $C_2$ are the corresponding coefficients of the fitting surface in the wet hydrogen sulfide environment method, $t_2$ is the hydrogen charging time of the wet hydrogen sulfide environment method, and $C_{H2S}$ is the hydrogen sulfide concentration of the solution in the wet hydrogen sulfide environment method.

According to yet another aspect of the disclosure, a method for assessing hydrogen damage to pipeline steel using the above hydrogen charging model for pipeline steel in an equivalent wet hydrogen sulfide environment is provided, and the method is specifically:

(a) The hydrogen charging model for pipeline steel in the equivalent wet hydrogen sulfide environment is used, and according to the hydrogen sulfide concentration of the target wet hydrogen sulfide environment, the hydrogen charging time and current density of the equivalent cathode hydrogen charging method is determined.

(b) According to the parameters determined in Step (a), the cathode hydrogen charging method is used to perform hydrogen charging on the pipeline steel to be tested to obtain an equivalent hydrogen charging pipeline steel.

(c) Hydrogen damage assessment is performed on the equivalent hydrogen charging pipeline steel, so as to be equivalent to the hydrogen damage of the pipeline steel in the target wet hydrogen sulfide environment.

In general, the above technical solution conceived by the disclosure has the following beneficial effects compared with the related art:

1. The method for establishing the hydrogen charging model for pipeline steel in the equivalent wet hydrogen sulfide environment provided by the disclosure has the advantages of simple operation, small volume of instruments and equipment used, and low cost, which can greatly reduce the cost of hydrogen charging related experiments for pipeline steel and is helpful for studying the hydrogen damage mechanism of pipeline steel under engineering and laboratory conditions. At the same time, the model obtained can greatly improve the test efficiency of for pipeline steel, and ensure that the highly toxic gas hydrogen sulfide does not need to be used in subsequent hydrogen damage assessment tests for pipeline steel, thereby the safety of test personnel and equipment are ensured and harm to the environment is not caused.

2. In particular, the disclosure optimizes the method for measuring the hydrogen content of the first hydrogen charging sample and the second hydrogen charging sample, which can further simplify the model establishment process while ensuring the measurement accuracy, and the relevant test costs are reduced.

3. At the same time, the disclosure provides a method for assessing hydrogen damage to pipeline steel using the established model. The method uses the cathode hydrogen charging method to provide equivalence for the hydrogen charging behavior of pipeline steel in the wet hydrogen sulfide environment, thereby efficient research and safe and rapid assessment of hydrogen damage to pipeline steel are achieved, and it is not required to use hydrogen sulfide gas. Compared with the method in the related art that requires simulating a wet hydrogen sulfide environment, the disclosure has the advantages of simple operation, safety and reliability, and high test efficiency.

BRIEF DESCRIPTION OF THE DRAWINGS

Throughout the drawings, the same reference numerals are used to denote the same elements or structures, in which.

1: negative electrode, 2: positive electrode, 3: test sample, 4: platinum electrode, 5: working electrode, 6: reference electrode, 7: auxiliary electrode.

DESCRIPTION OF THE EMBODIMENTS

In order to make the purpose, technical solutions, and advantages of the disclosure more comprehensible, the disclosure is further described in detail below together with the accompanying drawings and embodiments. It should be understood that the specific embodiments described herein are only used to explain the disclosure, and the embodiments are not used to limit the disclosure.

Figure 1:
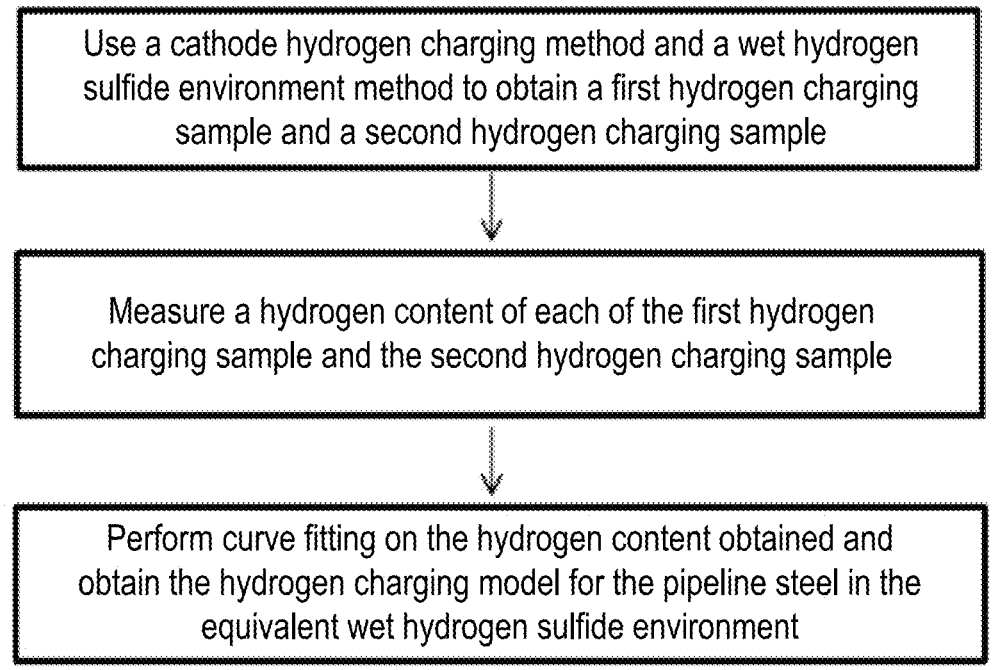
FIG. 1 is a flow chart of establishing a hydrogen charging model for pipeline steel in an equivalent wet hydrogen sulfide environment according to an embodiment of the disclosure.

As shown in FIG. 1, according to an aspect of the disclosure, a method for establishing a hydrogen charging model for pipeline steel in an equivalent wet hydrogen sulfide environment is provided, and the establishment method includes the following steps:

S1: test samples are taken from the pipeline steel used in the test and processed to obtain a plurality of samples to be tested, and then the cathode hydrogen charging method and the wet hydrogen sulfide environment method are respectively to perform hydrogen charging on each sample to be tested under different reaction conditions to obtain a plurality of first hydrogen charging samples and second hydrogen charging samples, in which the cathode hydrogen charging method uses different hydrogen charging times and current densities, and the wet hydrogen sulfide environment method uses different hydrogen charging times and hydrogen sulfide concentrations.

S2: The hydrogen content of each of the first hydrogen charging sample and the second hydrogen charging sample is measured, preferably an electrochemical method is adopted for measurement.

S3: According to the hydrogen content obtained in Step S2, curve fitting is performed on the variables in the two methods respectively, and according to the fitting results, a hydrogen charging model for pipeline steel in an equivalent wet hydrogen sulfide environment is obtained.

Further, in Step S1, the method for obtaining the sample to be tested is: a plurality of test samples are taken from the pipeline steel used in the test, and it is ensured that the thickness direction of each of the test samples is parallel to the diameter direction of the pipeline steel during sampling. Then, the test samples are ultrasonically cleaned in acetone and anhydrous ethanol to obtain the samples to be tested. At the same time, the sample to be tested is pretreated before oxygenation, specifically: a side of the sample to be tested in the thickness direction (that is, a surface perpendicular to the thickness direction) is connected to a wire through conductive glue, another side is sanded with sandpaper, and then polished with polishing paste until there is no scratch on the surface. Then, the whole sample to be tested is sealed with epoxy resin, and only the polished surface and the wire connector are exposed.

Further, in Step S1, the wet hydrogen sulfide environment method is specifically: the test solution is deoxygenated. Then, the sample to be tested is placed in a test solution in a closed environment, and hydrogen sulfide gas is introduced into the test solution with a preset hydrogen charging time and hydrogen sulfide concentration, so as to perform hydrogen charging with wet hydrogen sulfide on the sample to be tested. The test solution is preferably NACE-A solution, that is, 5% NaCl and 0.5% $CH_3COOH$ aqueous solution by mass, and the purity of the introduced $H_2S$ gas is greater than or equal to 99.5%.

The cathode hydrogen charging method is specifically: the sample to be tested as a cathode is placed in an electrolyte solution, and cathode hydrogen charging is performed at a preset hydrogen charging time and current density, in which the positive electrode of the constant current meter is connected to a platinum electrode, and the negative electrode is connected to the sample to be tested.

Further, in Step S2, an electrochemical method is adopted for measuring the hydrogen content, specifically: the change of the anode current of the sample not charged with hydrogen is measured, and used as the background current curve; then, the anode current change of each of the first hydrogen charging sample and the second hydrogen charging sample under the same conditions is tested respectively, and performed interpolation calculation with the area of the background current curve to obtain the hydrogen content of each of the first hydrogen charging sample and the second hydrogen charging sample. In the operation, the calculation formula of hydrogen concentration C is:

$$C = Q_{abs}/Fv \tag{1}$$

In the formula, $Q_{abs}$ is the total amount of hydrogen absorbed by the test sample, F is the Faraday constant (96487 C/mol), and v is the effective volume of the test sample.

Further, in Step S3, the least square method is used to perform curve fitting, in which the fitting result obtained by the cathode hydrogen charging method is:

$$C_{H1} = A_1 t_1^{0.5} + B_1 i^{0.5} + C_1 \tag{2}$$

In the formula, $C_{H1}$ is the hydrogen concentration of the first hydrogen charging sample obtained by the cathode hydrogen charging method, $A_1$, $B_1$, and $C_1$ are the corresponding coefficients of the fitting surface in the cathode hydrogen charging method, $t_1$ is the hydrogen charging time of the cathode hydrogen charging method, and i is the current density of the cathode hydrogen charging method.

The fitting result obtained by the wet hydrogen sulfide environment method is:

$$C_{H2} = A_2 t_2^{0.5} + B_2 C_{H2S}^{0.5} + C_2 \tag{3}$$

In the formula, $C_{H2}$ is the hydrogen concentration of the second hydrogen charging sample obtained by the wet hydrogen sulfide environment method, $A_2$, $B_2$, and $C_2$ are the corresponding coefficients of the fitting surface in the wet hydrogen sulfide environment method, $t_2$ is the hydrogen charging time of the wet hydrogen sulfide environment method, and $C_{H2S}$ is the hydrogen sulfide concentration of the solution in the wet hydrogen sulfide environment method.

The two fitting results are combined to obtain the hydrogen charging model for pipeline steel in the equivalent wet hydrogen sulfide environment, specifically:

$$\begin{cases} C_{H1} = A_1 t_1^{0.5} + B_1 i^{0.5} + C_1 \\ C_{H2} = A_2 t_2^{0.5} + B_2 C_{H2S}^{0.5} + C_2 \end{cases} \tag{4}$$

According to another aspect of the disclosure, a hydrogen charging model for pipeline steel in an equivalent wet hydrogen sulfide environment established by the above method is provided, and the model is specifically:

$$\begin{cases} C_{H1} = A_1 t_1^{0.5} + B_1 i^{0.5} + C_1 \\ C_{H2} = A_2 t_2^{0.5} + B_2 C_{H2S}^{0.5} + C_2 \end{cases} \tag{4}$$

In the formula, $C_{H1}$ is the hydrogen concentration of the first hydrogen charging sample obtained by the cathode hydrogen charging method, $A_1$, $B_1$, and $C_1$ are the corresponding coefficients of the fitting surface in the cathode hydrogen charging method, $t_1$ is the hydrogen charging time of the cathode hydrogen charging method, i is the current density of the cathode hydrogen charging method, $C_{H2}$ is the hydrogen concentration of the second hydrogen charging sample obtained by the wet hydrogen sulfide environment method, $A_2$, $B_2$, and $C_2$ are the corresponding coefficients of the fitting surface in the wet hydrogen sulfide environment method, $t_2$ is the hydrogen charging time of the wet hydrogen sulfide environment method, and $C_{H2S}$ is the hydrogen sulfide concentration of the solution in the wet hydrogen sulfide environment method.

In order to achieve equivalent hydrogen charging during use, $C_{H1}$ is equal to $C_{H2}$, so:

$$t_1 = \{[(A_2 t_2^{0.5} + B_2 C_{H2S}^{0.5} - B_1 i^{0.5}) + (C_2 - C_1)]/A_1\}^2, \quad (5)$$

alternatively $$i = \{[(A_2 t_2^{0.5} + B_2 C_{H2S}^{0.5} - A_1 t_1^{0.5}) + (C_2 - C_1)]/B_1\}^2 \quad (6)$$

According to the above formula, the hydrogen charging time of the cathode hydrogen charging method may be obtained under the target wet hydrogen sulfide environment and when the current density of the cathode hydrogen charging method is determined, or the current density of the cathode hydrogen charging method may be obtained under the target wet hydrogen sulfide environment and when the hydrogen charging time of the cathode hydrogen charging method is determined.

According to yet another aspect of the disclosure, a method for assessing hydrogen damage to pipeline steel using the above hydrogen charging model for pipeline steel in an equivalent wet hydrogen sulfide environment is provided, and the method is specifically:

(a) The hydrogen charging model for pipeline steel in the equivalent wet hydrogen sulfide environment is used, and according to the hydrogen sulfide concentration of the target wet hydrogen sulfide environment, the hydrogen charging time and current density of the equivalent cathode hydrogen charging method is determined.

(b) According to the parameters determined in Step (a), the cathode hydrogen charging method is used to perform hydrogen charging on the pipeline steel to be tested to obtain an equivalent hydrogen charging pipeline steel, thereby the equivalent hydrogen charging pipeline steel is obtained.

(c) Hydrogen damage assessment is performed on the equivalent hydrogen charging pipeline steel, so as to be equivalent to the hydrogen damage of the pipeline steel in the target wet hydrogen sulfide environment.

Pipeline steel produces hydrogen damage such as hydrogen induced cracking (HIC) and sulfur induced stress corrosion cracking (SSCC) in a wet hydrogen sulfide environment, so the safety performance assessment of pipeline steel is very important. Currently, the simulated wet hydrogen sulfide environment test is not only cumbersome and costly, but the hydrogen sulfide gas used also poses a huge safety hazard to test personnel and the environment. The method according to the disclosure uses the cathode hydrogen charging method to provide equivalence for the hydrogen charging behavior of pipeline steel in the wet hydrogen sulfide environment, thereby efficient research and safe and rapid assessment of hydrogen damage to pipeline steel are achieved, and it is not required to use the highly toxic gas hydrogen sulfide, which can better ensure the safety of test personnel and equipment, does not cause harm to the environment, and is helpful for studying the hydrogen damage mechanism of pipeline steel under engineering and laboratory conditions.

The technical solution provided by the disclosure is further described below based on specific embodiments.

Step 1: A thin slice sample is taken from the pipeline steel used in the test, and after processing, the sample to be tested is obtained.

In the specific implementation, the material selection is carried out first: X65 pipeline steel base material is selected, and the mechanical properties of the material are shown in the following table.

TABLE 1

| | Mechanical properties of pipeline steel base material | |
|---|---|---|
| Material | Yield strength (MPa) | Tensile strength (MPa) |
| X65 | 501 | 588 |

When sampling, it is ensured that the thickness direction is parallel to the diameter direction of the pipeline. The size of the thin slice sample is 10×10×2 mm. After sampling, the sample is ultrasonically cleaned respectively in acetone and anhydrous ethanol for 15 minutes.

Figure 2:
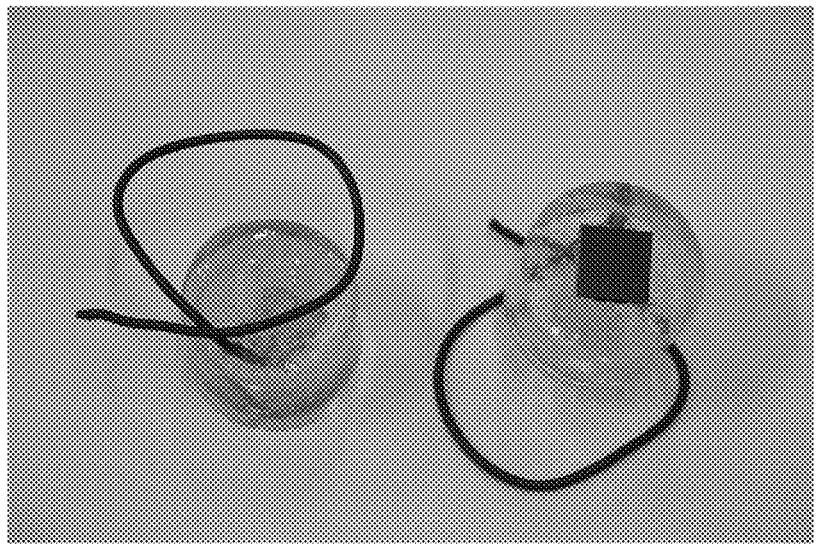
FIG. 2 is a schematic diagram of samples to be tested according to an embodiment of the disclosure.

Then, the thin slice sample is connected to a wire on a side in the thickness direction through conductive glue, and another side is sanded to 2000# with sandpaper, and then polished with polishing paste with a particle size of 2.5 μm until there is no scratch on the surface. The whole thin slice sample is sealed with epoxy resin, and only the polished surface and the wire connector are exposed, thereby the sample to be tested as shown in FIG. 2 is obtained.

Step 2: The cathode hydrogen charging method is used to perform hydrogen charging on each sample to be tested under different reaction conditions to obtain several first hydrogen charging samples, in which the sample to be tested is connected to the negative electrode of the constant current meter and placed in an acidic solution for cathode hydrogen charging. During the test, the time gradient and current density gradient are respectively controlled.

Figure 3:
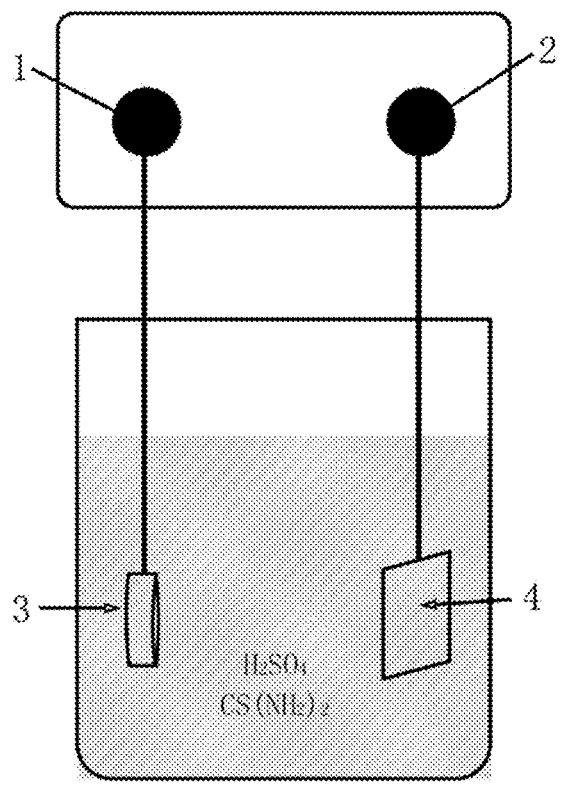
FIG. 3 is a schematic diagram of a cathode hydrogen charging method according to an embodiment of the disclosure.

As shown in FIG. 3, for samples of different sizes and materials, the solution used in the cathode hydrogen charging process may vary. For the X65 thin slice sample used in the test, the solution used is a mixed solution of 0.5 mol/L sulfuric acid and 1 g/L thiourea. A positive electrode 2 of the constant current meter is connected to a platinum electrode 4, and a negative electrode 1 is connected to a sample 3. In the test environment, the temperature is: 24±3° C., and the pressure is: 0.1 MPa.

Under the above test conditions, shown as follows:
(1) $t_1$=2 h, i=10, 20, 40, 80 mA/cm²;
(2) $t_1$=4 h, i=10, 20, 40, 80 mA/cm², the two sets of parameters are selected to perform cathode hydrogen charging.

Step 3: The wet hydrogen sulfide environment method is used to perform hydrogen charging on each sample to be tested under different reaction conditions to obtain a second hydrogen charging sample, in which the controlled variables in the test are respectively time and hydrogen sulfide concentration.

The hydrogen charging in the wet hydrogen sulfide environment is carried out according to the standard NACE MR0175-2015, NACE-A solution is adopted, that is, 5% NaCl and 0.5% $CH_3COOH$ aqueous solution by mass, and the purity of the introduced $H_2S$ gas is greater than or equal to 99.5%. The test environment is consistent with cathode hydrogen charging.

Hydrogen charging in the wet hydrogen sulfide environment requires a corrosion-resistant closed container, which includes an air inlet, an air outlet, a liquid inlet, and a liquid drain. Before introducing $H_2S$ gas into the solution, nitrogen gas with a purity of 99.5% is introduced into the solution at a nitrogen flow rate of 100 ml/min for 1 hour to remove oxygen.

After the $H_2S$ gas is introduced, the $H_2S$ concentration in the solution is measured using the iodine titration method in NACE TM0177-2016. Under the above test conditions, shown as follows:

(1) $C_{H2S}$=1500 mg/L, $t_2$=1, 2, 3, 4, 6, 8 days;
(2) $C_{H2S}$=2000 mg/L, $t_2$=1, 2, 3, 4, 6, 8 days;
(3) $C_{H2S}$=2500 mg/L, $t_2$=1, 2, 3, 4, 6, 8 days, the three sets of parameters are selected to perform hydrogen charging in the wet hydrogen sulfide environment.

Figure 4:
FIG. 4 is a schematic diagram of a wet hydrogen sulfide environment method according to an embodiment of the disclosure.

The wet hydrogen sulfide environment method is shown in FIG. 4.

Step 4: The electrochemical method is adopted to measure hydrogen content of each of the first hydrogen charging sample and the second hydrogen charging sample.

Figure 5:
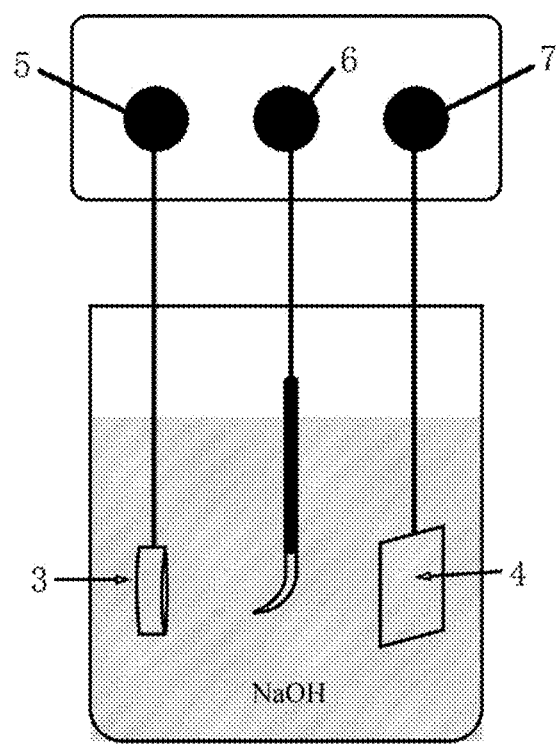
FIG. 5 is a schematic diagram of an electrochemical method for measuring hydrogen concentrations according to an embodiment of the disclosure.

As shown in FIG. 5, the solution used for the electrochemical method for measuring the hydrogen concentration is a 0.2 mol/L sodium hydroxide solution, a working electrode 5 is connected to the test sample 3, a reference electrode 6 is connected to the saturated calomel electrode, an auxiliary electrode is connected to the platinum electrode 4, the electrochemical comprehensive tester provides an anode potential of +0.3V, and the change of an anode current I is recorded in real time within 30 minutes. After hydrogen charging, the test sample should be quickly transferred to the sodium hydroxide solution. The test environment is consistent with cathode hydrogen charging and wet hydrogen sulfide environment hydrogen charging.

It is necessary to measure the change of the anode current of the sample not charged with hydrogen under the same condition. The data is used as the background current curve. The hydrogen concentration of the material under the set parameters is calculated based on the interpolation of the area included in the current curve before and after hydrogen charging. The calculation formula is:

$$C = Q_{abs}/Fv \quad (1)$$

$$Q_{abs} = \int (I_{charged\ with\ hydrogen} - I_{not\ charged\ with\ hydrogen})dt \quad (7)$$

In the formula, $Q_{abs}$ is the total amount of hydrogen absorbed by the test sample, F is the Faraday constant (96487 C/mol), and v is the effective volume of the test sample (0.2 cm$^3$ in the test).

The calculated hydrogen concentrations of the cathode hydrogen charging and hydrogen sulfide hydrogen charging test samples (unit: $10^{-6}$ mol/cm$^3$) are as follows:

TABLE 2

Hydrogen content of the first hydrogen charging sample

| Current density i (mA/cm$^2$) | 10 | 20 | 40 | 80 |
|---|---|---|---|---|
| $t_1$ = 2 h | 1.14058 | 1.56927 | 2.53146 | 3.7598 |
| $t_1$ = 4 h | 0.783 | 1.677 | 2.983 | 4.761 |

TABLE 3

Hydrogen content of the second hydrogen charging sample

| $t_2$ (days) | 1 | 2 | 3 | 4 | 6 | 8 |
|---|---|---|---|---|---|---|
| $C_{H2S}$=1500 mg/L | 0.502 | 1.887 | 1.092 | 1.625 | 6.116 | 9.689 |
| $C_{H2S}$=2000 mg/L | 1.460 | 1.158 | 1.491 | 2.990 | 13.859 | 9.717 |
| $C_{H2S}$=2500 mg/L | 1.689 | 2.388 | 4.160 | 9.711 | 11.364 | 16.950 |

Step 5: The least square method is used to perform curve fitting on the obtained result, and according to the fitting formula, the time or current density required for cathode hydrogen charging to achieve equivalence with a given wet hydrogen sulfide environment is calculated.

Respectively according to:

$$C_{H1} = A_1 t_1^{0.5} + B_1 i^{0.5} + C_1 \quad (2)$$

$$C_{H2} = A_2 t_2^{0.5} + B_2 C_{H2S}^{0.5} + C_2 \quad (3)$$

Fitting is performed on the hydrogen concentrations of cathode hydrogen charging and hydrogen charging in the wet hydrogen sulfide environment, in which $C_{H1}$ is the hydrogen concentration of the first hydrogen charging sample obtained by the cathode hydrogen charging method (unit: $10^{-6}$ mol/cm$^3$), $C_{H2}$ is the hydrogen concentration of the second hydrogen charging sample obtained by the wet hydrogen sulfide environment method (unit: $10^{-6}$ mol/cm$^3$), $t_1$ is the hydrogen charging time of the cathode hydrogen charging method (unit: hours), $t_2$ is the hydrogen charging time of the wet hydrogen sulfide environment method (unit: days), i is the current density of the cathode hydrogen charging method (unit: mA/cm$^2$), $C_{H2S}$ is the hydrogen sulfide concentration of the solution in the wet hydrogen sulfide environment method (unit: mg/L), $A_1$, $A_2$, $B_1$, $B_2$ are the corresponding coefficients of the fitting surface, and $C_1$ and $C_2$ are the constant terms of the fitting surface. The obtained fitting surfaces are:

$$CH_1 = 0.93 t_1^{0.5} + 0.58 i^{0.5} - 2.508 \quad (8)$$

$$CH_2 = 7.88 t_2^{0.5} + 0.37 C_{H2S}^{0.5} - 25.356 \quad (9)$$

Figure 6:
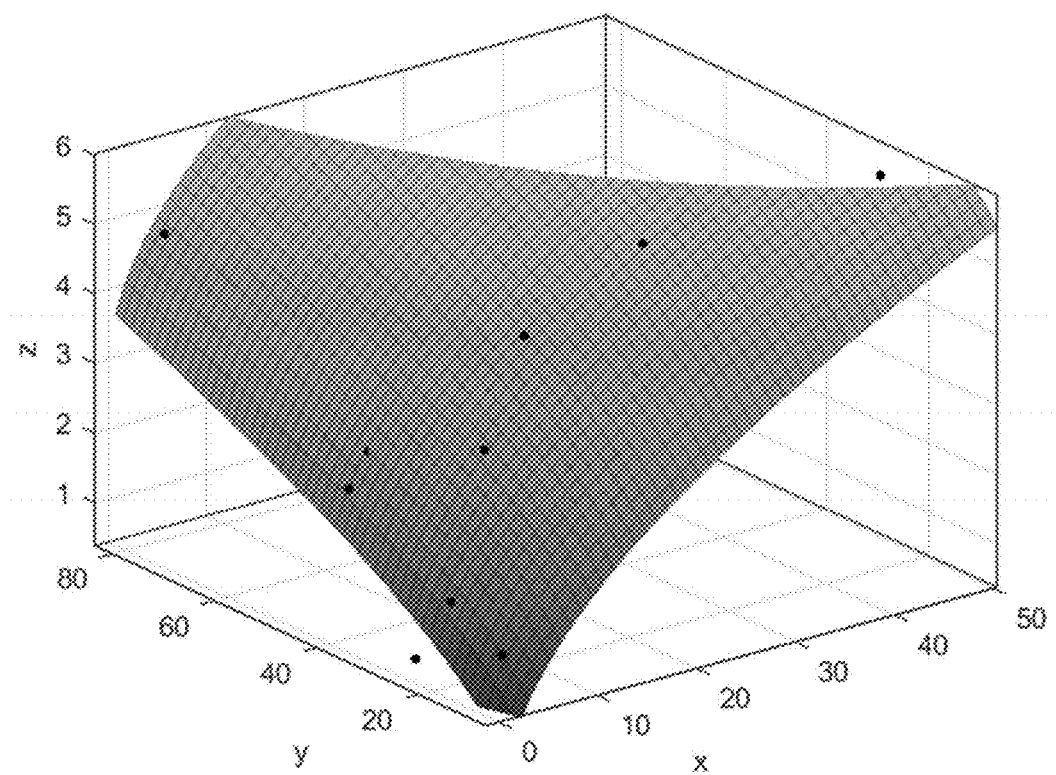
FIG. 6 is a fitting surface of the hydrogen charging concentration of the cathode hydrogen charging method according to an embodiment of the disclosure.
Figure 7:
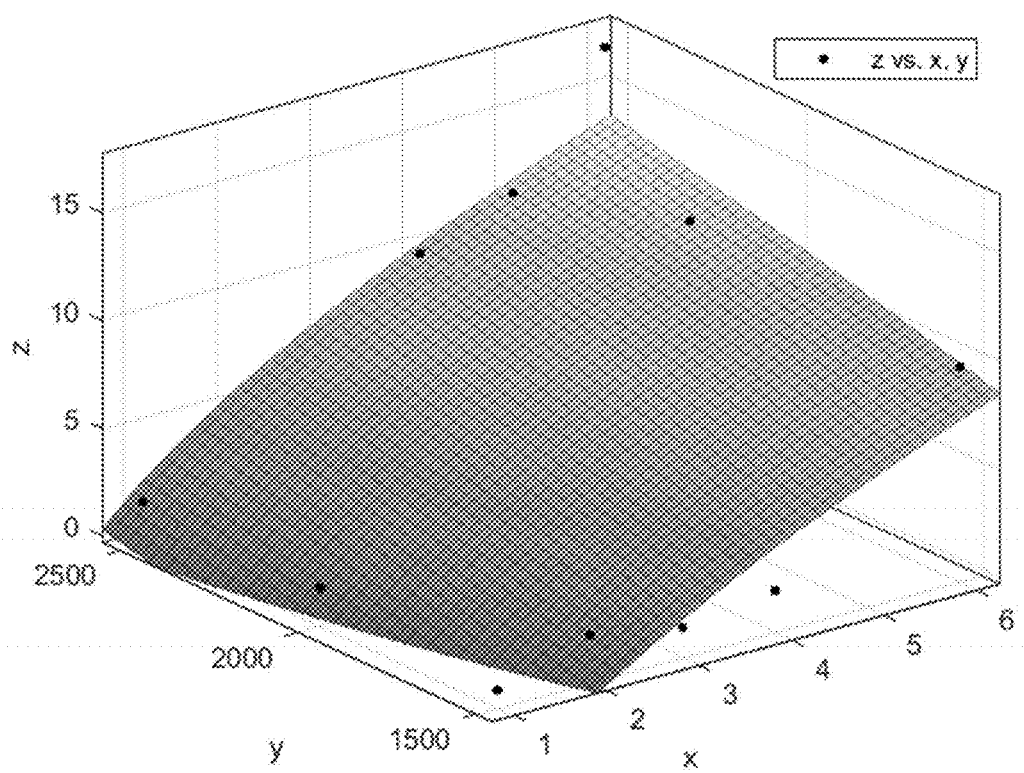
FIG. 7 is a fitting surface of the hydrogen charging concentration in the wet hydrogen sulfide environment method according to an embodiment of the disclosure.

The fitting curves of hydrogen charging concentrations for the cathode hydrogen charging method and the wet hydrogen sulfide environment method are respectively shown in FIG. 6 and FIG. 7.

Also, the final formula is obtained:

$$t_1 = [(7.88 t_2^{0.5} + 0.37 C_{H2S}^{0.5} - 0.58 i^{0.5} - 22.848)/0.93]^2, \quad (10)$$

alternatively $$i = [(7.88t_2^{0.5} + 0.37C_{H2S}^{0.5} - 0.93t_1^{0.5} - 22.848)/0.58]^2 \quad (11)$$

The output on the left side of Formula (10) is the time required for cathode hydrogen charging to achieve equivalence with the target wet hydrogen sulfide hydrogen charging, and the output on the left side of Formula (11) is the current density required for cathode hydrogen charging to achieve equivalence with the target wet hydrogen sulfide.

Step 6: The above formulas are used to determine the relevant parameters of cathode hydrogen charging achieving equivalence with the target wet hydrogen sulfide environment.

In this embodiment, the target wet hydrogen sulfide environment is: solution hydrogen sulfide concentration is 1800 mg/L, the hydrogen charging time is 4 days, and it is desired that a similar hydrogen charging effect can be obtained after 4 hours of cathode hydrogen charging. Substituting the above into Formula (11) for calculation, it is obtained that the current density should be selected as 33.6 mA/cm².

It should be easily understood by persons skilled in the art that the above description is only preferred embodiments of the disclosure and the embodiments are not intended to limit the disclosure. Any modifications, equivalent substitutions, and improvements made within the spirit and principles of the disclosure should be included in the protection scope of the disclosure.

What is claimed is:

1. A method for establishing a hydrogen charging model for pipeline steel in an equivalent wet hydrogen sulfide environment, wherein the establishment method comprises the following:

S1: using a cathode hydrogen charging method and a wet hydrogen sulfide environment method respectively to perform hydrogen charging on each sample to be tested under different reaction conditions to obtain a plurality of first hydrogen charging samples and second hydrogen charging samples, wherein the cathode hydrogen charging method specifically comprises: placing the sample to be tested as a cathode in an electrolyte solution, and performing cathode hydrogen charging at a preset hydrogen charging time and a current density;

S2: measuring a hydrogen content of each of the first hydrogen charging samples and the second hydrogen charging samples, and adopting an electrochemical method for measuring the hydrogen content, specifically: measuring an anode current change of a sample not charged with hydrogen, and using it as a background current curve; then, testing the anode current change of each of the first hydrogen charging samples and the second hydrogen charging samples under the same conditions respectively, and performing interpolation calculation on the anode current change of each of the first hydrogen charging samples and the second hydrogen charging samples with an area of the background current curve to obtain the hydrogen content of each of the first hydrogen charging samples and the second hydrogen charging samples;

S3: performing curve fitting on variables in the two methods respectively according to the hydrogen content obtained in Step S2, and obtaining the hydrogen charging model for the pipeline steel in the equivalent wet hydrogen sulfide environment according to a fitting result, wherein the hydrogen charging model for the pipeline steel in the equivalent wet hydrogen sulfide environment is specifically:

$$\begin{cases} C_{H1} = A_1 t_1^{0.5} + B_1 i^{0.5} + C_1 \\ C_{H2} = A_2 t_2^{0.5} + B_2 C_{H2S}^{0.5} + C_2 \end{cases}$$

wherein in the formula, $C_{H1}$ is the hydrogen concentration of the first hydrogen charging samples obtained by the cathode hydrogen charging method, $A_1$, $B_1$, and $C_1$ are the corresponding coefficients of the fitting surface in the cathode hydrogen charging method, $t_1$ is the hydrogen charging time of the cathode hydrogen charging method, i is the current density of the cathode hydrogen charging method, $C_{H2}$ is the hydrogen concentration of the second hydrogen charging samples obtained by the wet hydrogen sulfide environment method, $A_2$, $B_2$, and $C_2$ are the corresponding coefficients of the fitting surface in the wet hydrogen sulfide environment method, $t_2$ is the hydrogen charging time of the wet hydrogen sulfide environment method, and $C_{H2S}$ is the hydrogen sulfide concentration of the solution in the wet hydrogen sulfide environment method.

2. The method for establishing the hydrogen charging model for the pipeline steel in the equivalent wet hydrogen sulfide environment according to claim 1, wherein in Step S1, the method for obtaining the sample to be tested is: taking a plurality of test samples from the pipeline steel, and ensuring that a thickness direction of each of the test samples is parallel to a diameter direction of the pipeline steel during sampling; then, cleaning the test samples ultrasonically in acetone and anhydrous ethanol to obtain the samples to be tested.

3. The method for establishing the hydrogen charging model for the pipeline steel in the equivalent wet hydrogen sulfide environment according to claim 1, wherein in Step S1, the sample to be tested is pretreated, specifically: a surface of the sample to be tested is connected to a wire, and another surface is polished; then, the whole is sealed, and only the polished surface and a wire connector are exposed.

4. The method for establishing the hydrogen charging model for the pipeline steel in the equivalent wet hydrogen sulfide environment according to claim 1, wherein in Step S1, the wet hydrogen sulfide environment method is specifically: placing the sample to be tested in a test solution in a closed environment, and introducing hydrogen sulfide gas into the test solution at the preset hydrogen charging time and the hydrogen sulfide concentration so as to implement hydrogen charging in the wet hydrogen sulfide environment.

5. The method for establishing the hydrogen charging model for the pipeline steel in the equivalent wet hydrogen sulfide environment according to claim 1,
   wherein in Step S3, a least squares method is used to perform curve fitting.

6. A method for assessing hydrogen damage to pipeline steel using the method for establishing the hydrogen charging model for the pipeline steel in the equivalent wet hydrogen sulfide environment according to claim 1, wherein the method comprises the following:
   (a) using the hydrogen charging model for the pipeline steel in the equivalent wet hydrogen sulfide environment, and determining a hydrogen charging time and a current density of an cathode hydrogen charging method according to a hydrogen sulfide concentration of a target wet hydrogen sulfide environment;

(b) performing hydrogen charging on pipeline steel to be tested using the cathode hydrogen charging method according to the parameters determined in Step (a) to obtain an hydrogen charging pipeline steel;

(c) performing a hydrogen damage assessment on the hydrogen charging pipeline steel, so as to be equivalent to the hydrogen damage of the pipeline steel in the target wet hydrogen sulfide environment.

* * * * *